US00PP13814P39

(12) United States Plant Patent
Alvarado

(10) Patent No.: US PP13,814 P3
(45) Date of Patent: May 13, 2003

(54) DRACAENA PLANT NAMED 'DR9901ART'

(76) Inventor: Arturo Fernandez Alvarado, PO Box 310-3000, Heredia (CR)

( * ) Notice: Subject to any disclaimer, the term of this patent is extended or adjusted under 35 U.S.C. 154(b) by 0 days.

(21) Appl. No.: 10/050,938

(22) Filed: Jan. 22, 2002

(65) Prior Publication Data

US 2002/0133862 P1 Sep. 19, 2002

(51) Int. Cl.[7] ..... A01H 5/00
(52) U.S. Cl. ..... Plt./383

(58) Field of Search ..... Plt./383

*Primary Examiner*—Bruce R. Campell
*Assistant Examiner*—Annette H. Para
(74) *Attorney, Agent, or Firm*—Foley & Lardner

(57) ABSTRACT

A distinct Dracaena plant named 'DR9901ART' characterized by its relatively compact plant growth; leaves which are of an average length of 44 cm and an average width of 7.2 cm; distinctive leaf color with a yellow-green margin RHS 144A to RHS 144B, leaf width approximately 8 mm, a leaf center which is darker than but closes to green between RHS 137A and RHS 139A.

2 Drawing Sheets

BACKGROUND OF THE INVENTION

The present invention comprises a new and distinct cultivar of Dracaena plant botanically known as *Dracaena Vand.* Ex. *L. deremensis* and hereinafter referred to by the cultivar name 'DR9901ART'.

The new cultivar was selected by the inventor, Arturo Fernandez Alvarado, in Heredia, Costa Rica in 1997. The new cultivar was obtained as a natural mutation (as a sport) of *Dracaena Vand.* Ex. *L. deremensis* 'Lemon Lime' (unpatented).

The new cultivar was first asexually propagated by the inventor in Heredia, Costa Rica, in July 1997. Subsequent asexual reproduction of the new cultivar by division has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and in combination distinguish 'DR9901ART' as a new and distinct cultivar:

1. Dark green leaves with yellow margin;
2. Tough and tick leaves;
3. Fast and vigorous growth habit; and
4. Good resistance to adverse conditions.

'DR9901ART' has not been observed under all possible environmental conditions. The phenotype on the new cultivar may vary significantly with variations in environment such as temperature, light intensity, and day length without any change in genotype. The following observations, measurements and values describe plants grown in Honselersdijk, the Netherlands under normal commercial greenhouse conditions which closely approximate those generally used in horticultural practice.

In comparison with the well-known Dracaena cultivar 'Lemon Lime', 'DR9901ART' has leaves with more color and relatively more solid green. The leaves of 'Lemon Lime' have a broader yellow margin and thinner and paler green main color. The yellow margin is a unique golden/yellow shade, which is unlike the colors found in the leaves of any other *Dracaena deremensis* cultivar. The leaves of 'DR9901ART' are thicker and tougher which are much less susceptible to transportation, logistics and other damage than the leaves of 'Lemon Lime'. Compared to 'Lemon Lime', 'DR9901ART' is a faster and much more vigorously growing plant which is more resistant to adverse external conditions such as pests, diseases and climate. As a consequence, 'DR9901ART' is a more suitable cultivar to grow in adverse conditions, especially low light conditions.

BRIEF DESCRIPTION OF THE DRAWING

The accompanying photograph illustrates a 15 week old plant of 'DR9901ART' photographed in November, 2001 in Rijswijk, the Netherlands, with colors being as true as possible with illustrations of this type.

The first drawing shows the plant in its entirety.

The second drawing shows a close-up of the leaves of 'DR9901ART'.

DETAILED BOTANICAL DESCRIPTION

Color references are made to The Royal Horticultural Society Colour Chart (R.H.S.), except where general colors of ordinary significance are used. Colors are approximate as color depends on horticultural practices such as light level and fertilization rate, among others.

Classification:
*Botanical.*—*Dracaena Vand.* Ex. *L. deremensis.*
*Commercial.*—Dracaena cv DR9901ART.

Parentage: Mutant from *Dracaena deremensis* 'Lemon Lime'.

Propagation: Vegetative by taking cuttings of mother plant.

General observations:

*Growing conditions.*—In the Netherlands 'DR9901ART' is grown in a greenhouse under 20–21 degrees Celsius temperatures day and night. As with most Dracaena varieties, 'DR9901ART' does not stand direct sunlight so sun shields are closed when sunlight becomes too bright. No artificial lighting or photoperiodic treatments are conducted. Highest temperature resistance is at least 40 degrees Celsius, lowest is 5 degrees Celsius. Resistance, tolerance, and susceptibility to stresses, pathogens, and pests is very good. Compound fertilizer is added to the soil. There are no other cultural or environmental treatments.

*Plant vigor.*—Moderate.

Plant habit:

*Growth rate.*—2 cm per week.

*Form.*—Upright.

*Plant height.*—40 cm.

*Plant width.*—75 cm.

Leaves:

*Form and size.*—Ensiform to broad ensiform, average length: 44 cm, average width: 7.2 cm, tips bendt downward.

*Texture.*—Smooth, slightly glossy, furrowed at main vein.

*Vein.*—Parallel, main vein furrowed.

*Under side color.*—Margins irregularly striped vertically (average 8 mm) yellow-green, RHS 144A to RHS 144B. Leaf center green, between RHS 137A and RHS 146A.

*Upper side color.*—Margins irregularly striped vertically (average 8 mm) yellow-green, RHS 144A to RHS 144B. Leaf center green, closest to but darker than between RHS 137A and RHS 139A.

*Margin.*—Entire and only very slightly wavy.

*Thickness.*—Not very thick, moderately leathery.

*Number.*—Average of 7 leaves per 10 cm stem length.

Flowers: No inflorescences or flowers observed to date. Dracaenas only flower when the growing conditions are very poor (survival instinct of the plant).

Stem:

*Length.*—30 cm.

*Thickness.*—1.8 cm (on young shoots), older shoots grow thicker when aging.

*Color.*—Green, darker than RHS 139A.

Roots: Moderately branching, greyed-orange color, RHS 165B to RHS 167B. Time to initiate root development: 3 weeks after cutting Plant disease/insect tolerance: Not more susceptible to pests and diseases than similar varieties.

Reproductive organs: No reproductive organs observed to date.

I claim:

1. A new and distinct cultivar of Dracaena plant named 'DR9901ART', as described and illustrated herein.

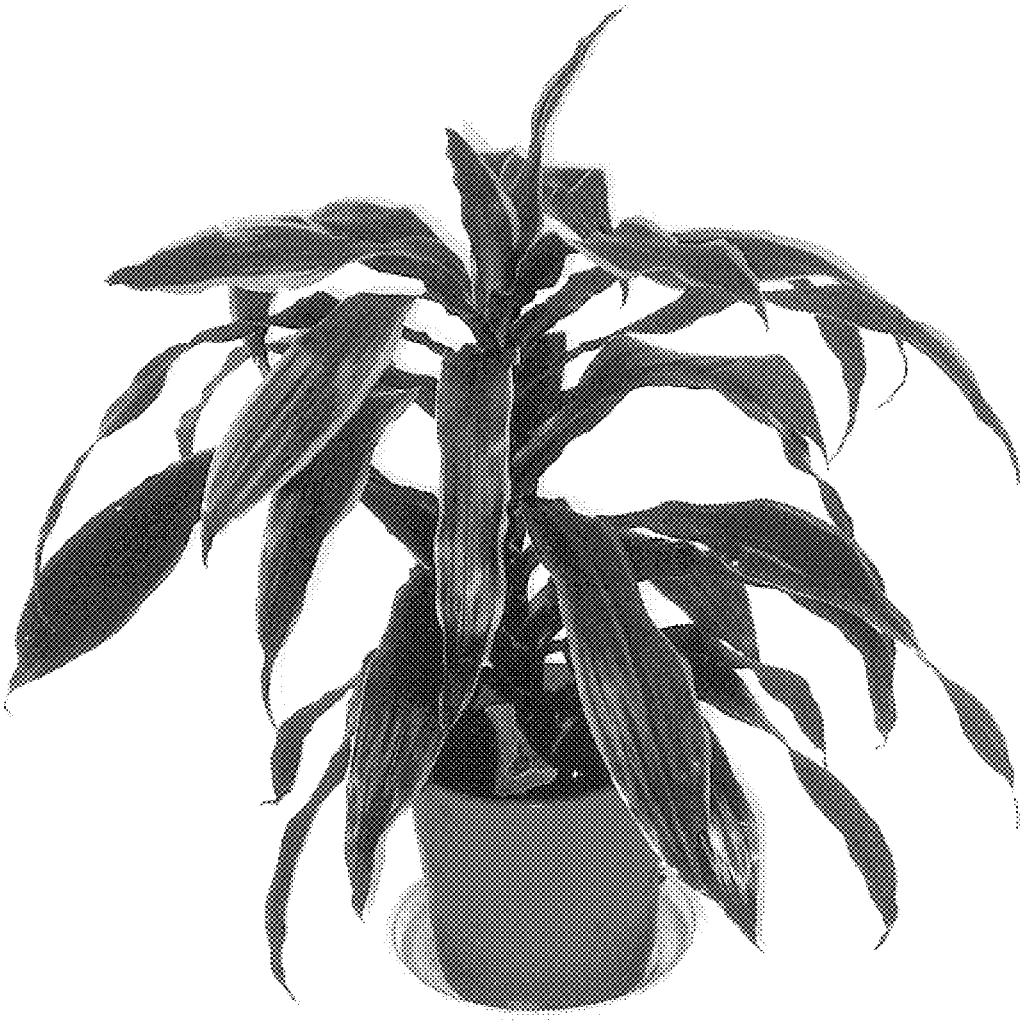

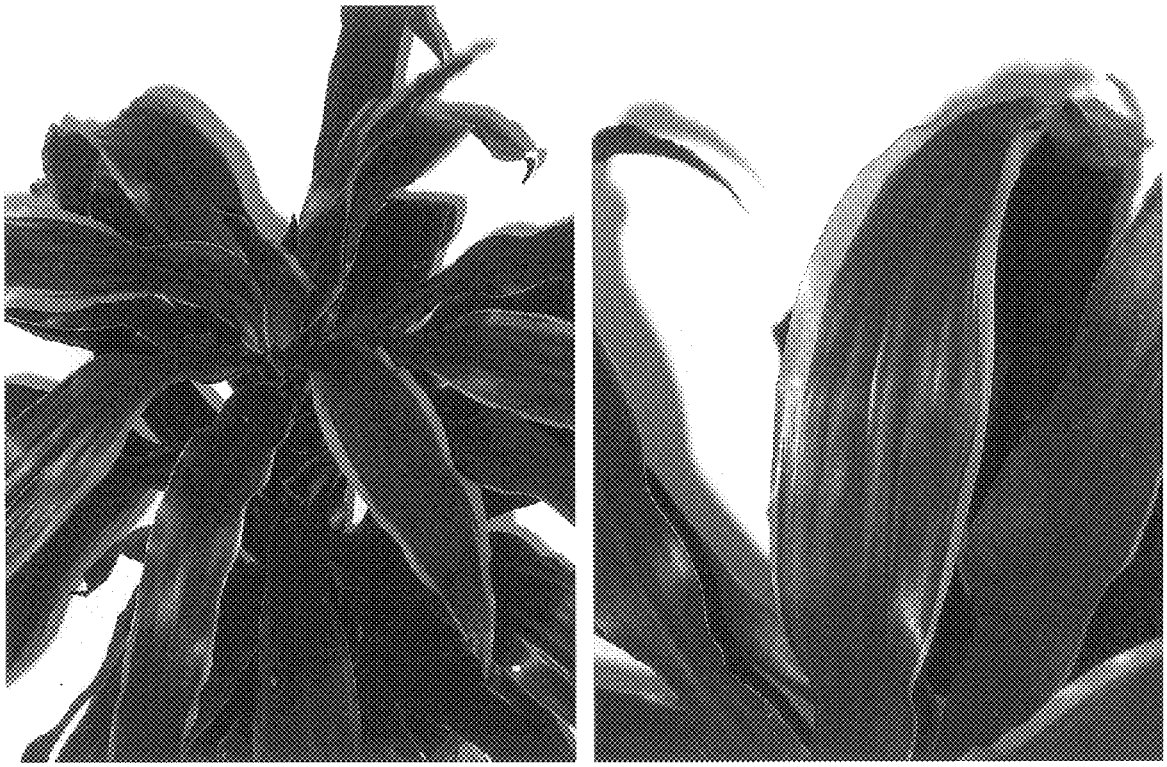

* * * * *